(12) United States Patent
Brain et al.

(10) Patent No.: US 6,406,469 B1
(45) Date of Patent: Jun. 18, 2002

(54) RE-USEABLE HOLDERS FOR DIAPERS AND DISPOSABLE LINERS

(76) Inventors: Lucille M. Brain, 254 Vause Lake Rd., Hawthorne, FL (US) 32640; Diane R. Dallavia, 1503 Leeward La., Neptune Beach, FL (US) 32233

( * ) Notice: Subject to any disclaimer, the term of this patent is extended or adjusted under 35 U.S.C. 154(b) by 0 days.

(21) Appl. No.: 09/544,985

(22) Filed: Apr. 7, 2000

(51) Int. Cl.[7] ................................................ A61F 13/15
(52) U.S. Cl. ..................................................... 604/394
(58) Field of Search ............................... 604/397, 358, 604/394, 392, 396, 393, 398, 400, 401

(56) References Cited

U.S. PATENT DOCUMENTS

| | | |
|---|---|---|
| 3,000,381 A | 9/1961 | Mulhole et al. |
| 3,483,864 A | 12/1969 | DeZacarias |
| 3,688,767 A | 9/1972 | Goldstein |
| 3,900,032 A | 8/1975 | Heurlen |
| 4,576,601 A | 3/1986 | Brain |
| 4,671,793 A * | 6/1987 | Hults et al. ............ 604/385.14 |
| 4,773,906 A * | 9/1988 | Krushel ...................... 604/391 |
| 4,846,815 A * | 7/1989 | Scripps ................ 128/DIG. 15 |
| 4,869,724 A * | 9/1989 | Scripps ........................ 604/389 |
| 4,963,140 A * | 10/1990 | Robertson et al. .......... 604/389 |
| 5,019,065 A * | 5/1991 | Scripps .................. 604/385.21 |
| 5,069,672 A * | 12/1991 | Wippler et al. ........ 604/385.14 |
| 5,217,447 A * | 6/1993 | Gagnon ......................... 2/400 |
| 5,984,911 A * | 11/1999 | Siebers et al. .............. 604/358 |
| 6,296,629 B1 * | 10/2001 | Siebers et al. .............. 604/386 |

FOREIGN PATENT DOCUMENTS

GB       1 520 740       8/1978

* cited by examiner

*Primary Examiner*—Danny Worrell
(74) *Attorney, Agent, or Firm*—Miles & Stockbridge P.C.; Dennis P. Clarke

(57) ABSTRACT

A diaper holder comprising a water-proof material having horizontal bands secured at the ends to form an open loop at the top and bottom below the waistbands to hold cloth diapers or liners securely in place. The lateral sides of the holder are in-curved and elasticized to form leg embracing openings. The waistbands are elastic and size adjustable with the use of releasable fasteners of hook and pile.

19 Claims, 5 Drawing Sheets

RE-USEABLE HOLDERS FOR DIAPERS AND DISPOSABLE LINERS

FIELD OF THE INVENTION

The present invention relates to reusable pantsiholders for diapers and disposable liners.

DESCRIPTION OF THE PRIOR ART

Pants that function as holders for diapers or disposable liners are well known in the prior art. Most suffer from one or more of several disadvantages such as, e.g., (1) the need to be secured on the wearer by safety pins or other external securing devices which can become lost or can injure the wearer; (2) are not reusable; (3) need to be unsecured or unfastened to remove the diaper or disposable liner; (4) have a construction, shape or conformation required for holding the diaper or liner that is uncomfortable to the wearer, and the like. Typical of such holders are those shown in U.S. Pat. Nos. 3,000,381; 3,483,864; 3,688,767; 3,900,032 and UK Patent No. 1,520,740.

Many of these disadvantages are overcome by the pants/holder described in U.S. Pat. No. 4,576,601 (the entire contents and disclosure of which are incorporated herein by reference). That patent discloses a plastic pants/holder for diapers fastenable by releasable hook/pile fasteners that securely fix a diaper or disposable liner in a desired position. Although that patents/holder represents a significant improvement over prior art garments of the same type, it nevertheless suffers from the disadvantage that the hook/pile fasteners must be released in order to remove the pants/holder from the wearer. The garment is of such a construction that, when the hook/pile fasteners are secured to hold the garment in place on the wearer, it can only be removed by releasing the fasteners.

It is an object of the present invention to provide an improved pants/holder of the type described in U.S. Pat. No. 4,576,601 that may be removed from the wearer without the necessity for releasing the hook/pile fasteners.

SUMMARY OF THE INVENTION

The above and other objects are realized by the present invention, one embodiment of which relates to a diaper or liner holder comprising a plastic piece extending between a back waistband portion and a front waistband portion along two sides; each waistband portion having two ends, each side having an elastic member to provide elastic contractable leg portions by gathering at least part of the side; front and back bands attached to the plastic piece to extend lengthwise along and adjacent to the respective front and back waistband portions and operable to hold a cloth diaper, liner or disposable pad placed over and under the bands; each of the waistband portions having a releasable hook/pile fastening portion at least at end of its ends; wherein the holder forms pants upon each of the fastening portions of the front waistband portion being secured to a complimentary one of the fastening portions of the back waistband portion with each of contractable leg portions defining a leg opening; each side having an overlapping portion disposed to overlap a corresponding overlapped portion of the same side, each overlapping portion removable relative to the corresponding overlapped portion from the leg opening up to the waistband portions such that air may circulate under the overlapping portions; wherein the fabric fastening portions on the waistbands are fastenable so as to adjust the diaper holder for different sized waists; and wherein the back and front waistband portions are elastic to permit the holder to be pulled down at least part way over the legs of the wearer and, if desired, to be pulled back up to its original position without the need to release the hook/pile fastening portions.

DETAILED DESCRIPTION OF THE INVENTION

The diaper or liner holder of the present invention enables one to put on the wearer a water-proof pants and diaper or disposable liner without the necessity for employing dangerous and inconvenient safety pins. Another benefit associated with the invention is a lessening of the deleterious impact imposed on the environment by present day disposable diapers. Thus, the plastic pants/holder is reusable.

The invention saves time in that the pants and diaper (or liner) may be put on at the same time rather than first installing the diaper and then pulling tight plastic pants over the diaper. If disposable liners are employed rather than cloth diapers, these are the only items that require disposal.

The holders of the invention wash and wear well and are ideal for toilet training. Also, they are easier to use for the handicapped. The principal benefits of the invention are the elimination of the inconvenience and danger of safety pins in attaching a cloth diaper to a baby and the use of tight plastic pants. The waist has an adjustable releasable closure of hook and pile and the bands at the back and front of the holder hold a standard cloth diaper securely without slipping when placed over and under the bands, giving more concentrated absorbency than conventional methods of pinning. The overlapping in the hip area on each side allows air to circulate with movement to deter diaper rash while the elastic in the leg openings prevents leakage.

The diaper holder is made of water-proof material such as vinyl sheeting, water-proof polymer coated fabric, or the like. The shape is generally rectangular, wider at the top than the bottom and in-curved in the center to permit passing through of the legs of the wearer. This area employs elastic tape by zig-zag stitching or equivalent technique to provide leg embracing portions; therefore, the leg embracing portions are extensive and elastic. The waistbands are made by folding the top and bottom edges over to form, e.g., double vinyl waistbands that are sewn, welded or glued. The waistband is adjustable to fit the waist size of the wearer by the use of strips of releasable closure of hook and pile and positioned at either end of the waistbands. Located directly below the waistbands are, e.g., double vinyl bands that may be sewn, glued or welded at each end to form open loops.

Figure 1:
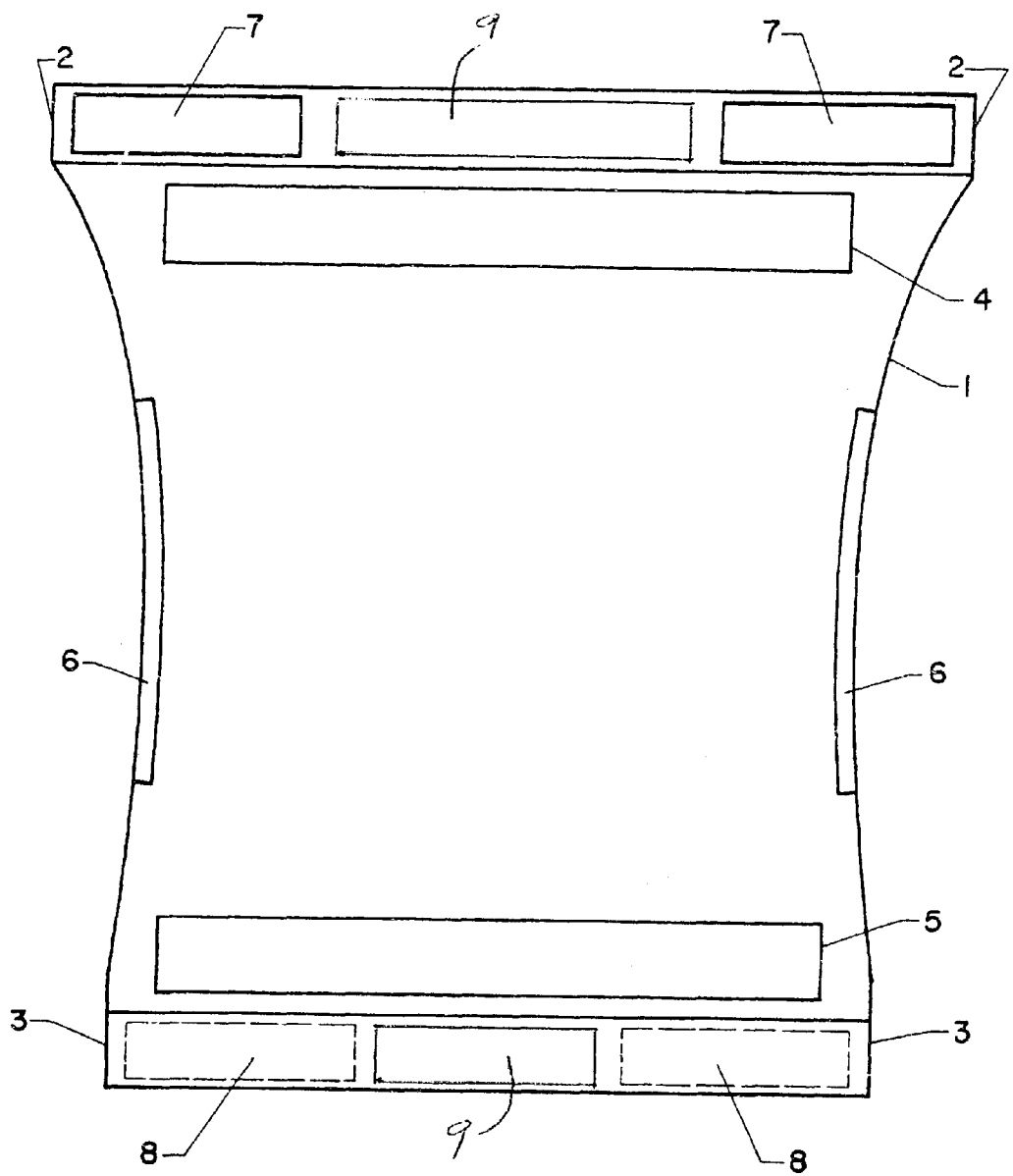
FIG. 1 is a perspective view of the invention showing the pants/holder.

Referring to FIG. 1, the holder or shell 1 is comprised of plastic resinous or plastic material to render the holder/pants water-proof. Top waistband 2 may be a double layer of (or doubled over) plastic material. Bottom waistband 3 is constructed similarly to top waistband 2. Strips 4 and 5, which may also be constructed of plastic material, are secured (e.g., by sewing) at their ends to the shell 1 to form open loops.

Strips 4 and 5 are also rendered elastic by, e.g., gathering a portion thereof. A portion 6 at each side of the shell 1 is rendered elastic (by, e.g., gathering) so as to form leg openings for the wearer when the holder is worn. Strips 7 of pile fastener are secured at both ends of the top waistband 2 in the inside thereof. Hook fasteners 8 are secured at both ends of the bottom waistband 3 on the outside thereof. Strips 9 between the fasteners 7 and 8 of top and bottom waistbands 2 and 3, respectively, are rendered elastic by, e.g., gathering so as to permit expansion of the waist portion of the holder when fastened in place on the wearer and at least partially removed therefrom when fasteners 7 and 8 are engaged.

Figure 2:
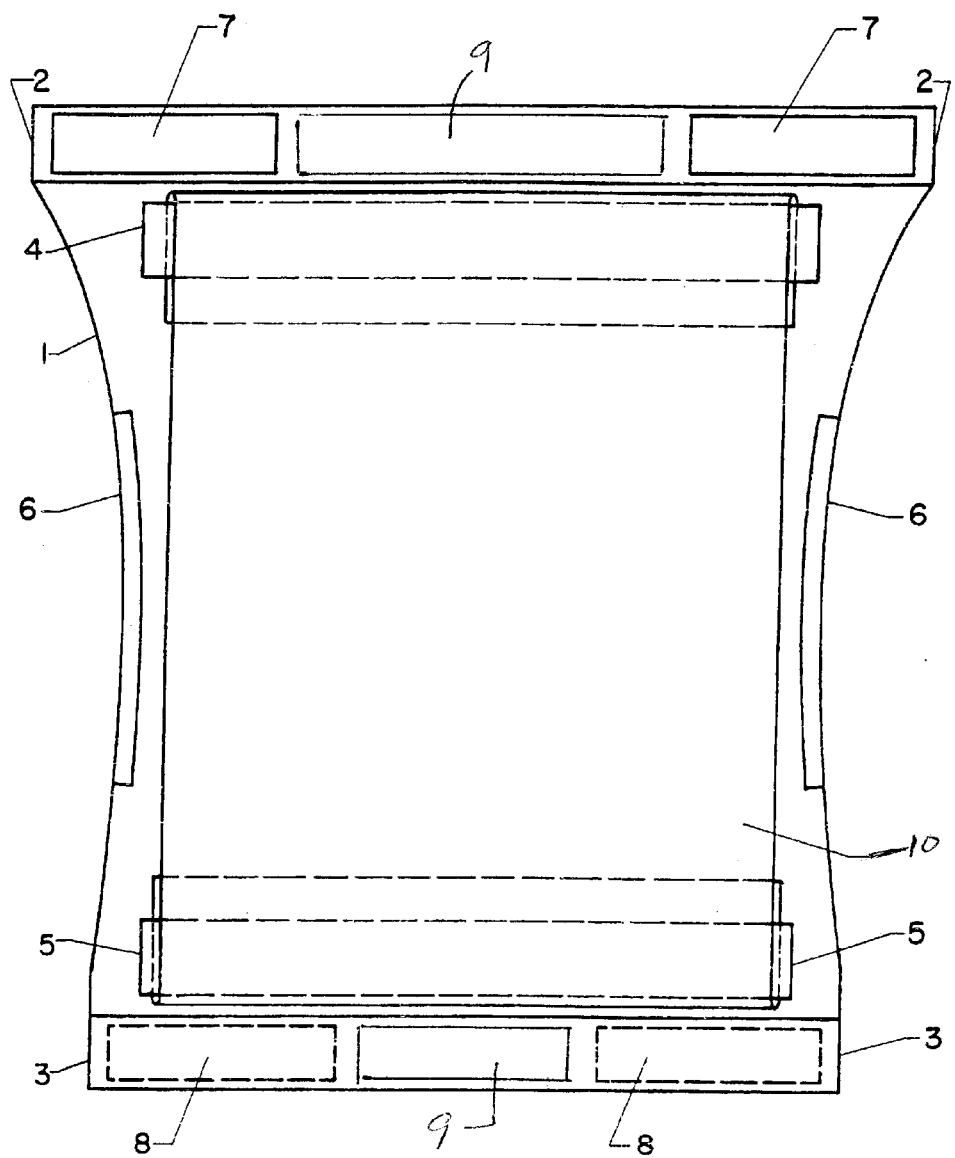
FIG. 2 is a perspective view of the invention showing the pants/holder and the contained diaper or liner.

FIG. 2 demonstrate how a cloth diaper or disposable liner 10 may be positioned up, over and under loops 4 and 5 to hold it securely in place when the holder 1 is fastened together by means of fasteners 7 and 8 to form pants.

Figure 3:
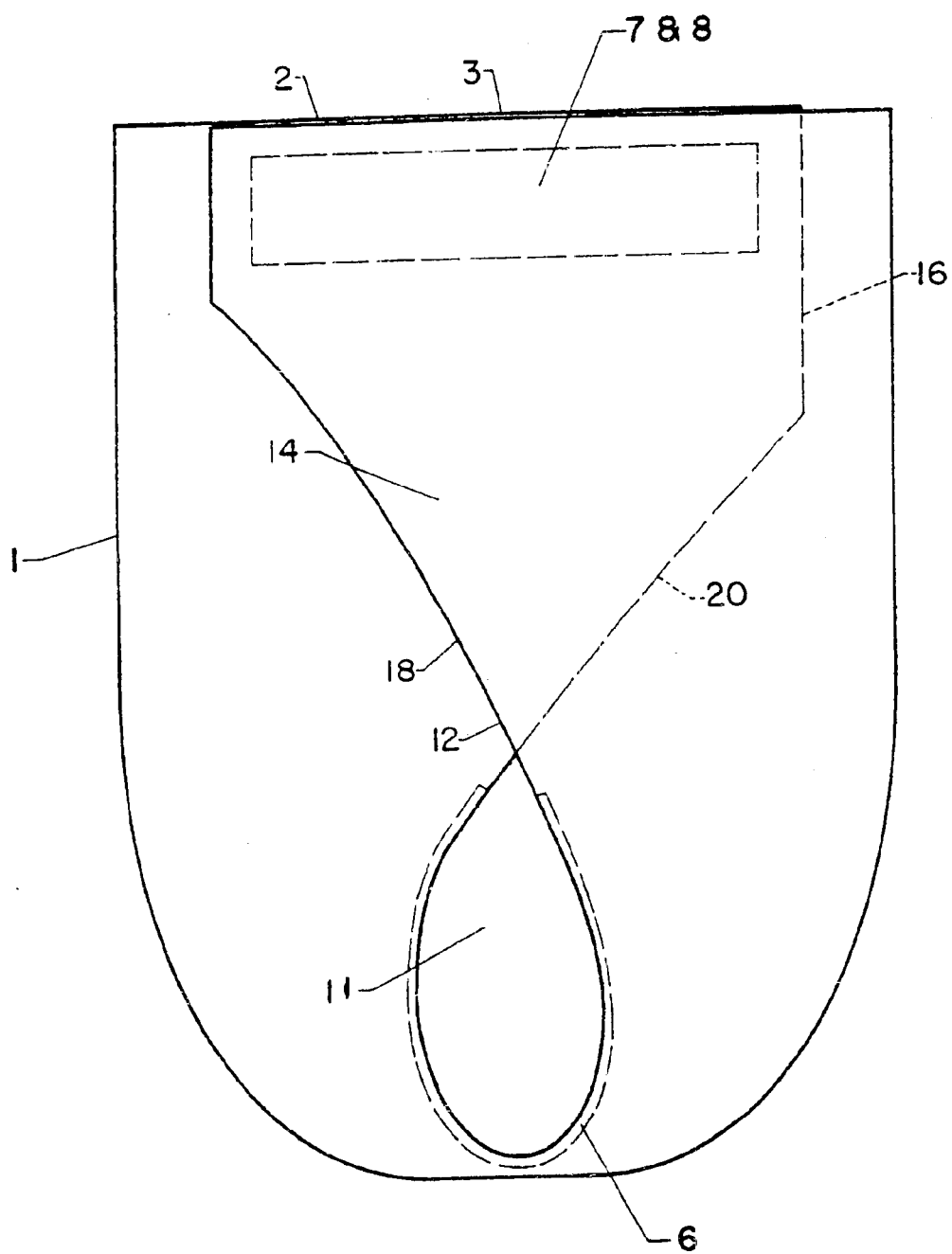
FIG. 3 is a side elevational view of the holder folded and fastened into pants.

FIG. 3 depicts the pants formed by bringing the top and bottom waistbands 2 and 3, respectively, together and securing them via fasteners 7 and 8 to form leg openings 11.

Figure 4:
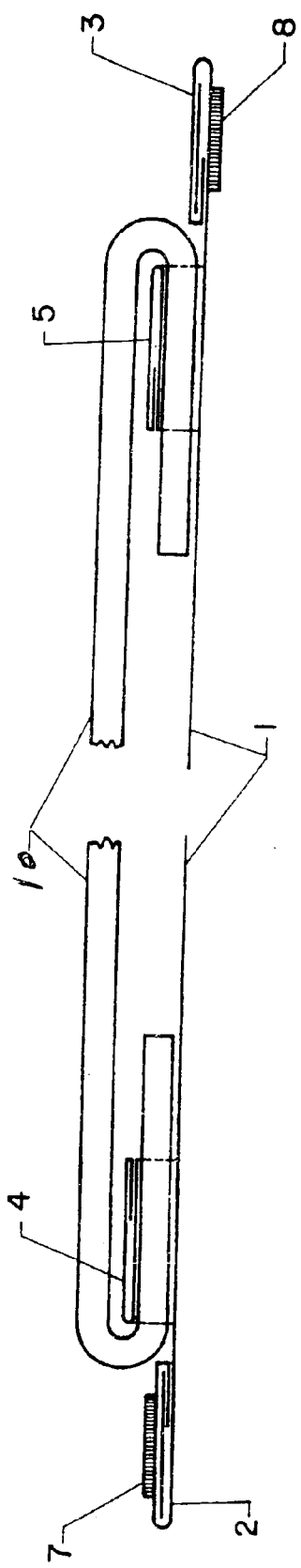
FIG. 4 is a side elevational view of the holder and contained diaper.

FIG. 4 depicts the holder from a side showing how the diaper 10 is secured in place via loops 4 and 5.

Figure 5:
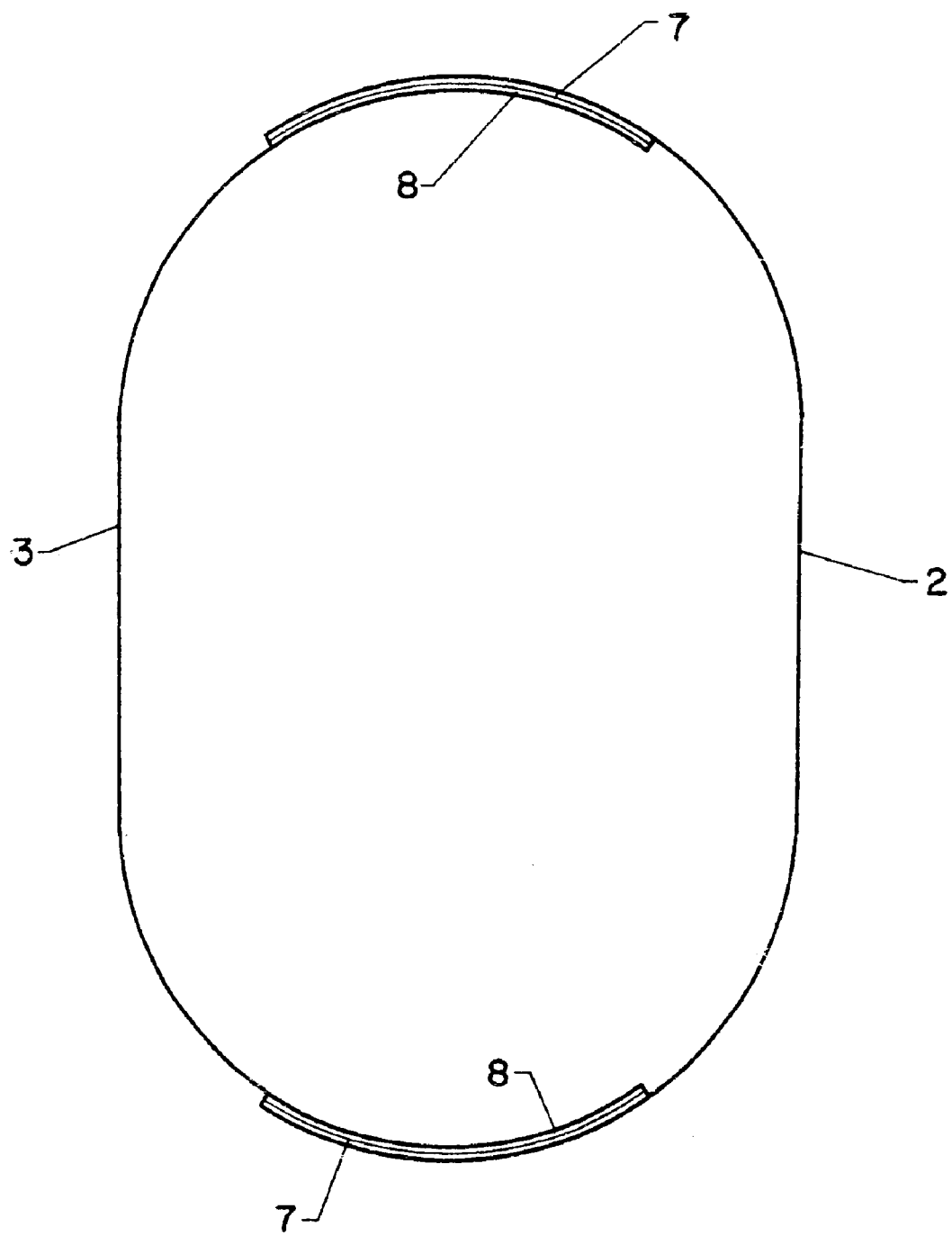
FIG. 5 is a top elevational view of the holder.

FIG. 5 depicts the holder viewed from the top when the waistbands 2 and 3 are secured together via fasteners 7 and 8.

As may be best appreciated from the view of FIG. 3, the diaper holder of the present invention forms pants upon each of the releasable hook/pile fabric fastening portions 7 and 8 of the front waistband portion (3 in FIG. 2) being secured to a complimentary one of the fastening portions of the back waistband portion (2 in FIG. 2). As shown, each of the contractable leg openings 6 defines a leg opening 11. Each of the sides 12 (see also FIGS. 1 and 2) has an overlapping portion 14 disposed to overlap a corresponding overlapped portion 16 of the same side 12. As will be readily appreciated from the position of fasteners 7 and 8 shown in FIG. 3, the overlapping portion 14 is movable relative to the corresponding overlapped portion 16 from the leg opening 11 up to the waistband portions 2 and 3. This arrangement with movable overlapping portions will most advantageously allow air to circulate under the overlapping portions. As shown, the overlapping portion 14 and the overlapped portion 16 have curved edges 18 and 20, respectively, which extend up from the corresponding leg opening 11.

As shown in FIGS. 1 and 2, each of the sides extending between the waistband portions 2 and 3 extend inwardly to narrow at a point intermediate the waistband portions. As shown in the drawings, the intermediate point is along the elastic contractable leg portions 6. Specifically, each side extends inwardly at least from each of the bands 4 and 5 to the intermediate point, as clearly sown in FIGS. 1 and 2. Each side is pointless from the back waistband portion 2 (top in FIGS. 1 and 2) to the front waistband portion 3 (low end of FIGS. 1 and 2), meaning that there are no sharp ends along this side. As shown, each of the sides has a continuous curve from the back waistband portion to at least the front diaper-holding band 5.

The holder as described above is essentially that of U.S. Pat. No. 4,576,601. The improvement thereover embodied by the present invention comprises the strips 9 in waistbands 2 and 3 that are elastic. This improvement allows the wearer (or another) to partially remove the pants/holder without unfastening fasteners 7 and 8. Thus, in applications where the wearer is an infant undergoing potty training, the child may simply pull down the pants to use the potty and simply pull them back up when finished without having to unfasten the hook and pile fasteners 7 and 8. Similarly, where the wearer is an incontinent elderly person, the latter need only pull down the pants when visiting the bathroom and need not unfasten the entire device to do so.

The holder/pants of U.S. Pat. No. 4,576,601 suffers from the disadvantage that the waistbands are inextensible, thereby requiring unfastening in order to even partially remove the device from the wearer. It will be readily apparent that the prior art device would not be as suitable for e.g., potty training and the like as that of the present invention.

As will be appreciated by those skilled in the art, strips 9 may be rendered elastic by way of a variety of means and methods. It is preferred to render the strips elastic by simply gathering the top and bottom waistbands where indicated.

It is also preferred to render strips 4 and 5 elastic (also by, e.g., gathering) to more frrmly secure the diaper or liner 10 in the loops formed thereby.

To use the holder of the invention, the diaper or liner is folded to the width desired, placed on the holder and tucked over and under the plastic loops on the top and bottom. The holder is positioned on the baby and the bottom end is pulled up between the legs. The larger top waistband is brought over the bottom waistband on each side and fastened with the hook and pile fasteners to fit the size for the baby's waist. This design has the necessary tightness in the legs, yet still lets air circulate, thereby deterring diaper rash.

While the above description contains many specifications, these should not be construed as limitations on the scope of the invention, but rather as an exemplification of one preferred embodiment thereof. Many other variations are possible, for example, they can be made in sizes for infants, children and adults, the mentally handicapped and the elderly. They can be used as a liner in the matching pants of diaper sets and pajama bottoms for infants. A one-inch wide length of elastic can be substituted for the plastic loops. Any other closing could be utilized as hooks, grippers, snaps, etc. The elastic could be gathered from just under the top waistband along the leg openings to just under the bottom waistband to give a tighter fit in the legs. An absorbent liner or diaper pad with adhesive strips on the back could be manufactured to fit. They could be stamped out of plastic with welded or laminated edges and waistbands or any other process available.

We claim:

1. A diaper or liner holder, said holder being reusable and consisting essentially of a plastic piece extending between a back waistband portion and a front waistband portion along two sides; each waistband portion having two ends, each side having an elastic member to provide elastic contractible leg portions by gathering at least part of the side; front and back bands attached to said plastic piece to extend lengthwise along and adjacent to said respective front and back waistband portions and operable to detachably hold a cloth diaper, liner or disposable pad placed over and under the bands; each of said waistband portions having a releasable hook/pile fastening portion at least at each of its ends; wherein said holder forms pants upon each of said fastening portions of said front waistband portion being secured to a complimentary one of said fastening portions of said back waistband portion with each of contractible leg portions defining a leg opening; each side having an overlapping portion disposed to overlap a corresponding overlapped portion of the same side, each overlapping portion removable relative to the corresponding overlapped portion from the leg opening up to the waistband portions such that air may circulate under the overlapping portions; wherein said fabric fastening portions on the waistbands are fastenable so as to adjust the diaper holder for different sized waists; and wherein said back and front waistband portions are elastic to permit the holder to be pulled down at least part way over the legs of the wearer and, if desired, to be pulled back up to its original position without the need to release said hook/pile fastening portions.

2. The holder of claim 1 wherein said back and front waistband portions are elastic by a gathering of at least a part thereof.

3. The holder of claim 1 wherein said front and back waistbands are elastic.

4. The holder of claim 3 wherein said font and back waistbands are elastic by a gathering of at least a part thereof.

5. The holder of claim 1 wherein said plastic piece comprises a fabric coated on the side adapted to fit against a wearer thereof with a water-proof coating.

6. The holder of claim 5 wherein said fabric comprises a nylon.

7. The holder of claim 5 wherein said water-proof coating comprises a polymeric coating.

8. The holder of claim 1 wherein said bands comprise a fabric coated with a waterproof coating.

9. The holder of claim 8 wherein said fabric comprises a nylon.

10. The holder of claim 8 wherein said water-proof coating comprises a polymeric coating.

11. The holder of claim 7 or 10 wherein said polymer is a vinyl polymer.

12. The holder of claim 1 wherein each of said waistband portions has a portion folded over to form a double thickness.

13. The holder of claim 12 further comprising a fabric reinforcing piece within the double thickness of each waistband portion.

14. The holder of claim 1 wherein each of said sides extends inwardly to narrow at a point intermediate the waistband portions.

15. The holder of claim 14 wherein each side extends inwardly from each band to the corresponding intermediate point.

16. The holder of claim 15 wherein each side is pointless from said front waistband portion to said back waistband portion.

17. The holder of claim 14 wherein each side has a continuous curve from one of said waistband portions to at least the other of said waistband portions.

18. The holder of claim 14 wherein, when the holder is formed into pants, each of said overlapped portions has a curved edge extending up from the corresponding leg opening and each of said overlapping portions has a curved edge extending up from the corresponding leg opening.

19. The holder of claim 1 wherein said fastening portions on said waistband portions are the only fasteners on the holder.

* * * * *